United States Patent [19]

Townsend

[11] 4,201,213

[45] May 6, 1980

[54] SURGICAL TOOL

[75] Inventor: Paul R. Townsend, Hull, Mass.

[73] Assignee: Codman & Shurtleff, Inc., Randolph, Mass.

[21] Appl. No.: 873,347

[22] Filed: Jan. 30, 1978

[51] Int. Cl.² .............................................. A61B 17/32
[52] U.S. Cl. .................................................. 128/312
[58] Field of Search ........................ 128/305, 310–318, 128/325, 329 R

[56] References Cited

U.S. PATENT DOCUMENTS

| 988,939 | 4/1911 | Hudson | 128/312 |
|---|---|---|---|
| 1,040,523 | 10/1912 | DeVilbiss | 128/312 |
| 2,555,133 | 5/1951 | Horstmann | 128/329 R |
| 3,752,161 | 8/1973 | Bent | 128/312 |
| 3,777,538 | 12/1973 | Weatherly et al. | 128/325 X |

FOREIGN PATENT DOCUMENTS

| 230503 | 1/1911 | Fed. Rep. of Germany | 128/312 |
|---|---|---|---|
| 24791 | 11/1902 | United Kingdom | 128/318 |

OTHER PUBLICATIONS

"Zimmer News Release"; Oct. 1966.
"Zimmer News Release"; Oct 11, 1966.

Primary Examiner—Richard J. Apley

[57] ABSTRACT

A surgical tool comprises a slidable member having a passage therethrough such as a substantially cylindrical hollow tube. The distal end of the slidable member serves as a first jaw component. An elongated member is positioned in the passage and has a second jaw component on its distal end adapted to oppose the first jaw component. A handle is connected to the slidable member for sliding the same over the elongated member to change the spacing between the first and second jaw components and to apply force to the object held between the jaw components.

4 Claims, 7 Drawing Figures

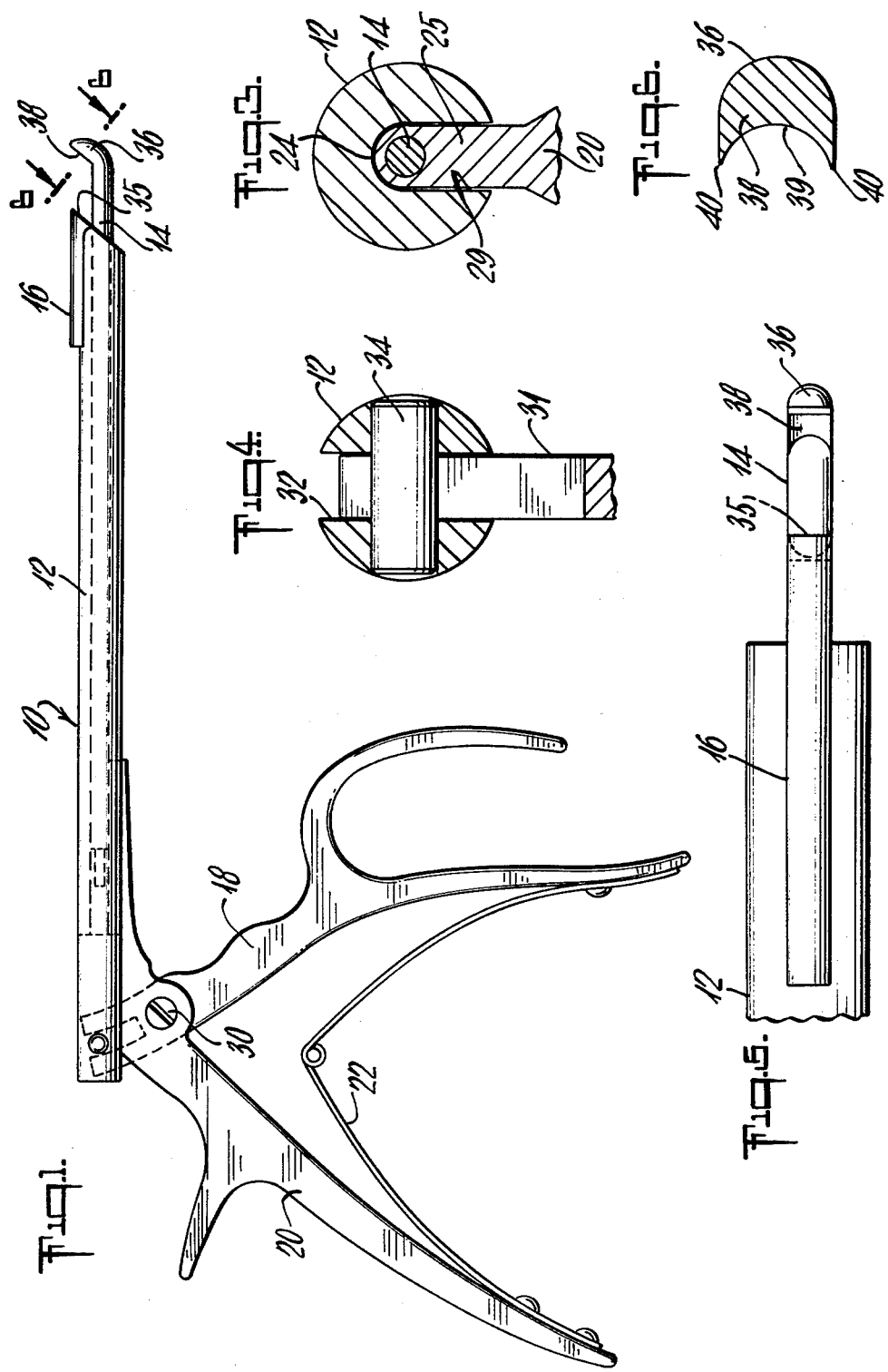

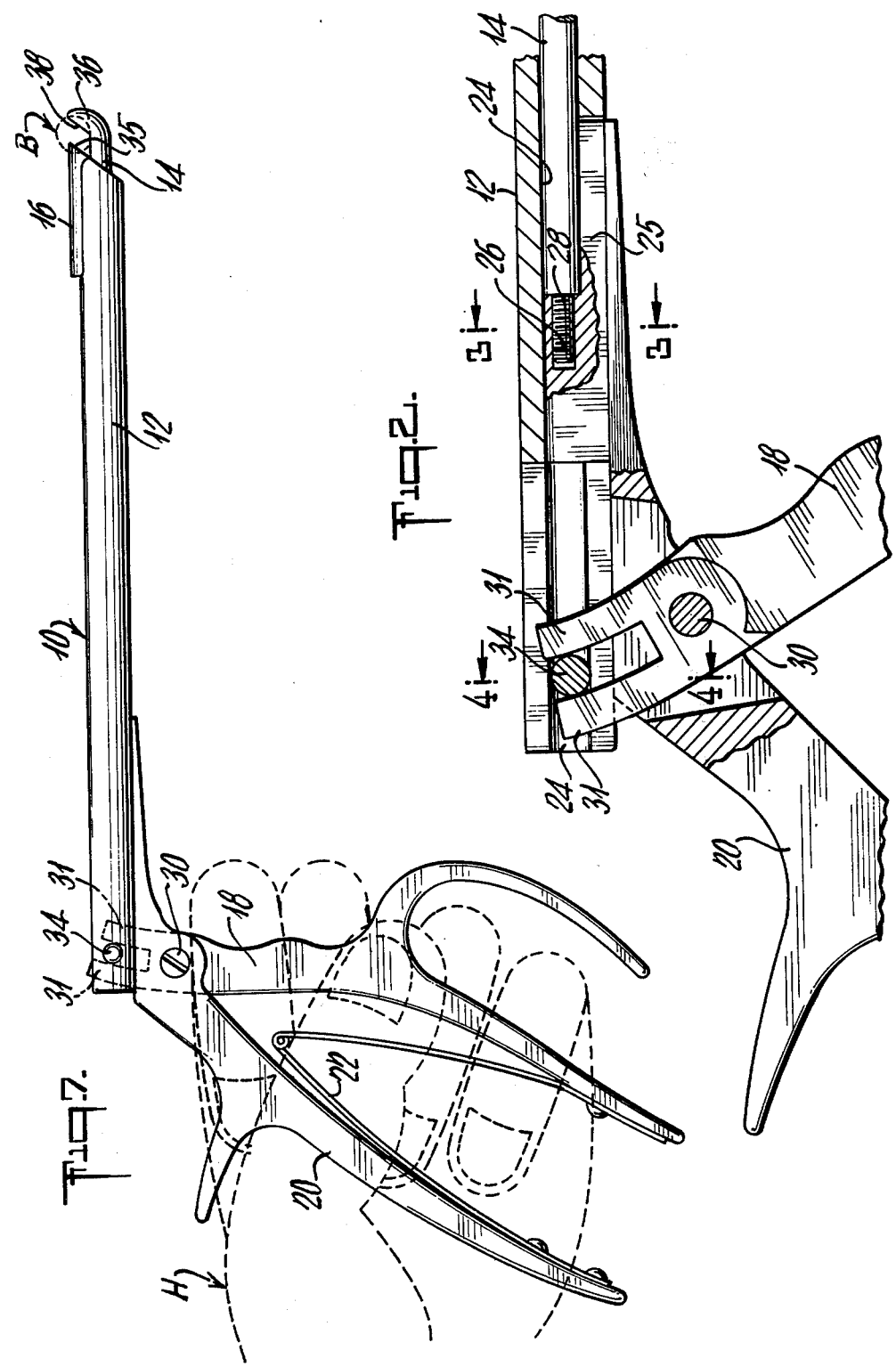

SURGICAL TOOL

BACKGROUND OF THE INVENTION

The present invention relates to a surgical tool useful by surgeons of varied disciplines, but particularly useful during surgery in cutting, gripping or perforating bones, soft tissues and the like.

Rongeurs and similar surgical tools have been known and employed by surgeons for gouging away bone during the surgical operation. Various rongeurs are adapted to cut, grip, chip or sometimes merely hold onto the bone structure or soft tissue as may be necessary. For cutting purposes, the known rongeurs have been fabricated with a jaw-like configuration at the end of an elongated body. These rongeurs provide for the jaws to be opened and closed, such as by plier-type gripping handles, by the ready manipulation by the surgeon. The elongated body allows the surgeon to reach into the surgical area where the cutting or gripping has to be performed.

In providing the open-close ability to the jaws of the known rongeurs, one jaw component has been constructed to slide relative to the other. Typical rongeurs such as found in U.S. Pat. No. 3,752,161 and in the Zimmer News Release of October, 1966, rely upon a T-slot configuration whereby a tongue on one slidable member slides in a groove in the other member, the ends of which form the cutting jaws. While this construction is satisfactory as far as functionability and imparting adequate strength to the jaws for the sometimes difficult bone cutting steps, there are some shortcomings also. For instance, bone chips, tissue or undesirable debris may enter the T-slot, which would cause the instrument to stick and possibly jam during the operation. In addition, the T-slot (tongue and groove) structure is limited in its strength. The typical tongue portion includes a somewhat narrow shank connected to the T-bar. Any unexpected and excessive lateral shear or bending forces transmitted along this tongue during a bone cutting operation may cause a structural failure, with the instrument being rendered useless. Accordingly, these deficiencies in the known rongeurs or like surgical tools indicate that there is room for further improvement.

SUMMARY OF THE INVENTION

A surgical tool comprises a slidable member having passage means therethrough, with the distal end of the slidable member serving as a first jaw component. An elongated member is positioned in the passage means and has a second jaw component on its distal end adapted to oppose the first jaw component. Means for sliding the slidable member over the elongated member is provided to change the spacing between the first and the second jaw components and to apply force to the object held between the jaw components.

In the preferred embodiment of the present invention, the slidable member is a substantially cylindrically shaped hollow tubular barrel and includes an insert attached to its distal end. The first jaw component is the outwardly facing end of the insert which has a cutting edge thereon. An elongated shaft is positioned in the passageway formed by the hollow tubular barrel, and the distal end of the shaft is upturned beyond the distal end of the barrel. On the inside face of the upturned end is another cutting edge which opposes the cutting edge on the insert in jaw-like fashion. A first handle movably connected to the barrel provides the means for sliding the same over the shaft. A second handle is fixedly connected to the shaft; the first handle is pivotally connected to the second handle so that squeezing of the handles toward each other decreases the spacing between the respective jaw-like cutting edges and applies force to the object held between the same.

From the structural standpoint, the surgical tool of the present invention is notably different from similar surgical tools in a number of respects. For instance, the present surgical tool employs a structure which is closely related to a piston slidably movable in a cylinder, rather than the T-slot structure which has been known and used previously. Advantageously, the present surgical tool is constructed to provide more material at the high stress points, thus decreasing the potential for breakage during the cutting or gripping operations. In addition, the tolerances between the sliding components and their surface smoothness can be fabricated to reduce the sticking problem by keeping debris away from the sliding areas.

BRIEF DESCRIPTION OF THE DRAWINGS

FIG. 1 is a plan view of the preferred surgical tool of the present invention;

FIG. 2 is an enlarged plan view partially broken away to illustrate the portion of the surgical tool which provides the sliding function;

FIG. 3 is an enlarged cross-sectional view taken along lines 3—3 of FIG. 2;

FIG. 4 is an enlarged cross-sectional view taken along lines 4—4 of FIG. 2;

FIG. 5 is a partial top view illustrating the distal end portion of the preferred surgical tool;

FIG. 6 is an enlarged cross-sectional view taken along lines 6—6 of FIG. 1; and

FIG. 7 is a plan view illustrating the preferred surgical tool being grasped during the gripping, cutting and the like operations.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a surgical tool 10 which is useful during surgery for cutting, gripping, holding and the like of bones or soft tissue. The general elements of surgical tool 10 include a slidable barrel 12, a shaft 14, an insert 16 attached to barrel 12, a first handle 18 connected to barrel 12, a second handle 20 connected to shaft 14 and a spring device 22 associated with handles 18 and 20 to allow the handles to return to their original positions after a gripping force is released.

Referring now to FIGS. 2-4, in conjunction with FIG. 1, barrel 12 is seen as a substantially cylindrically shaped hollow tube, the hollow portion forming a passageway 24 therethrough. Barrel 12 is generally elongated so as to provide the surgeon with the ability to reach into the area to perform the operation with this tool. In addition, barrel 12 is a slidable member which provides the opening and closing function for the gripping and cutting purposes. Passageway 24, normally a hole or bore extending completely therethrough for ease of fabrication, is desirably smooth surfaced and highly polished and also held to tight tolerances. In this regard, barrel 12 readily slides over shaft 14 which, in turn, slidably fits in passageway 24.

Shaft 14 is an elongated slender rod which also desirably has a smooth surface and high polish for compatibility with the sliding function. As seen especially in FIG. 2, shaft 14 is positioned in passageway 24 of the barrel and is anchored to a block 25 which is part of second handle 20. Block 25 is provided with an internal thread 26 which receives the mating threaded portion 28 at one end of shaft 14. In this manner, shaft 14 is fixedly connected to second handle 20 in addition to being inserted in passageway 24 of the barrel. Turning to FIG. 3, a slot 29 has been provided in barrel 12 so that block 25 may properly extend into the barrel to provide the attaching device for shaft 14. It is appreciated that the tolerances between slot 29 and the width of block 25 are tightly held so as to reduce any lateral play during sliding.

To provide the means for sliding barrel 12 over shaft 14, first handle 18 is pivotally connected to second handle 20, such as by pin 30 which connects the two handles together but allows rotative movement between them. At the upper end of first handle 18 there are two fork-like projections 31. Projections 31 are dimensioned to fit into a vertically aligned slot 32 in the proximal or rear end of barrel 12. This slot is large enough to allow rotative movement of projections 31 with handle 18 when it is squeezed to slide barrel 12. A dowel pin 34 is press fit in the rear end of barrel 12 in a substantially horizontal plane. During assembly of the components, projections 31 are slid into slot 32 so that pin 34 rests in between the two projections. Once again, the spacing between projections 31 and the diameter of pin 34 are relatively tightly toleranced so as to reduce excess play in the sliding movement of the barrel. It can be seen that squeezing of handles 18 and 20 toward each other moves projections 31 so that fixed pin 34 rides between them in the proximal end of the barrel, thus causing barrel 12 to slide over shaft 14.

Turning now to FIGS. 5 and 6, in conjunction with FIG. 1, it can be seen that insert 16 is attached to the distal end of barrel 12. This end, including insert 16, serves as a first jaw component for the cutting and gripping operations. Insert 16 is included in order to provide additional surface area to the jaw for increased strength during cutting and the like. Insert 16 also moves with barrel 12 when the jaws are drawn closer together. Accordingly, the insert serves as a movable support to provide additional strength to the barrel regardless of the space between the jaws after the object has been gripped. This extra strength is particularly desirable when the jaws are inclined at an angle as mentioned hereinafter. However, insert 16 is not essential if sufficient surface area on the distal end of barrel 12 can be provided for the specific function intended of the tool. The outwardly facing surface 35 at the end of the insert is a cutting section or edge which contacts the object, such as a bone, between the jaw components. While outwardly facing surface 35 preferably includes a cutting edge, it is appreciated that there are instances when mere gripping or holding of the bone can be accomplished without a cutting edge at all. It is also seen in FIG. 1 that outwardly facing surface 35 is forwardly inclined on an angle with respect to the longitudinal axis of the barrel. This angle provides a better grip on the bone or tissue, and serves to reduce any slippage of the tool after the object has been gripped.

Shaft 14 includes an upturned distal end 36 extending beyond the distal end of barrel 12. On the inside face of upturned end 36, in the preferred embodiment, is a cutting section or edge 38 which is inwardly facing so as to oppose outwardly facing surface 35, the cutting edges thereby facing each other in jaw-like fashion. Inwardly facing surface 38 is also preferably, but not necessarily, inclined to form an angle with respect to the longitudinal axis of the barrel. In this regard, the cutting edges, while inclined, are substantially parallel to each other in one plane so as to facilitate the required gripping function. One embodiment of the cutting edge on upturned end 36 is illustrated in FIG. 6. Inwardly facing surface 38 is formed with a concave surface 39 therein so as to produce a sharp cutting point or edge 40 at opposite ends of the upturned section of the shaft. Points 40 provide for solid gripping, especially of the bone, while allowing the cutting to occur in more than one location; this serves to better distribute the loading forces perceived by the upturned end of the shaft during the periods of highest stress. In addition, concave surface 39 serves as a depressed area to provide a cavity to receive bone chips or soft tissue which is being operated on. Although not shown, the cutting surface of outwardly facing edge 35 on insert 16 is substantially similar, in the preferred embodiment, to that shown in FIG. 6, except in the reverse orientation.

FIG. 7 more clearly illustrates the operation of surgical tool 10. The hand H of the surgeon grasps handles 18 and 20 which, in this case, are formed to provide a firm grip. Of course, the handle configurations may vary according to many different factors, including the specific surgical operation intended. It can be seen, however, that as the handles are squeezed by hand H toward each other, barrel 12 slides over shaft 14 to decrease the spacing between the jaw-like cutting edges 35 and 38. In this way the object to be gripped or cut, such as bone B, is located by the surgeon who squeezes the handles until it is firmly locked in place between the jaw-like surfaces. Further squeezing of the handles by the surgeon applies force to the bone and produces the cutting effect, if desired. When the gripping and/or cutting step is completed, the surgeon releases the grip on the handles so that spring 22, such as a two-piece leaf spring, urges handles 18 and 20 back to their original static position. This, in turn, slides the barrel back to increase the spacing between the respective cutting edges, thus releasing the grip on the object formally held.

Inasmuch as strength is an important factor in tools which are used for cutting purposes, it is preferred that the components of the present surgical tool be fabricated of metal. Stainless steel, such as medical grade stainless steel, is one example of the type of metal which can be used to fabricate this surgical tool. The stainless steel is receptive to a high polish, especially on those surfaces where sliding and pivoting movements are to be expected. In addition, the metal construction allows the insert at the end of the barrel to be welded in place so as to provide a more unitary structure while not sacrificing strength. While welding of the insert in position is preferred, depending upon the configuration of the insert, other fastening techniques may be employed.

Thus, it is apparent that there has been provided in accordance with the invention a surgical tool for cutting, gripping, holding and the like having a novel construction and providing the improvements as set forth above.

What is claimed is:

1. A surgical tool comprising: an elongated slidable barrel having a hollow passageway therethrough and having an outwardly facing cutting section on its distal end; an elongated shaft positioned in said passageway and having an inwardly facing cutting section on its distal end, said inwardly facing cutting section projecting beyond said distal end of said barrel, said cutting sections adapted to oppose each other in jaw-like fashion; and means for sliding said barrel over said shaft to change the spacing between said respective jaw-like cutting sections and to apply force to the object held between the same, said outwardly facing cutting section being formed on an insert, said insert being attached to said distal end of said barrel.

2. A surgical tool comprising: an elongated slidable, substantially cylindrically shaped barrel having a hollow passageway therethrough and including an insert attached to its distal end, said insert having an outwardly facing cutting edge thereon; an elongated shaft positioned in said passageway and having its distal end upturned beyond the distal end of said barrel, said upturned end having a cutting edge formed on its inside face so that said respective cutting edges oppose each other in jaw-like fashion; a first handle movably connected to said barrel and a second handle fixedly connected to said shaft, said first handle being pivotally connected to said second handle so that squeezing of said handles toward each other decreases the spacing between said respective jaw-like cutting edges and applies force to the object held between the same.

3. A surgical tool as defined in claim 2 wherein said cutting edges form an angle with respect to the longitudinal axis of said barrel.

4. A surgical tool as defined in claim 2 which further includes spring means between said handles so that said handles are returnable to their static positions when a gripping force is released.

* * * * *